(12) United States Patent
Brandigi

(10) Patent No.: US 7,662,159 B2
(45) Date of Patent: Feb. 16, 2010

(54) ANTIMICROBIAL TRANSCUTANEOUS ACCESS SHIELD AND KIT

(75) Inventor: Claus Brandigi, Augusta, GA (US)

(73) Assignee: AEK Medical, Inc., Augusta, GA (US)

( * ) Notice: Subject to any disclaimer, the term of this patent is extended or adjusted under 35 U.S.C. 154(b) by 0 days.

(21) Appl. No.: 11/965,462

(22) Filed: Dec. 27, 2007

(65) Prior Publication Data

US 2008/0161739 A1    Jul. 3, 2008

Related U.S. Application Data

(60) Provisional application No. 60/882,299, filed on Dec. 28, 2006.

(51) Int. Cl.
    *A61B 1/32*      (2006.01)
    *A61M 5/32*      (2006.01)

(52) U.S. Cl. ............... 606/108; 600/201; 600/208; 602/43; 602/60; 602/63; 604/174; 604/175; 604/265; 604/337

(58) Field of Classification Search ............ 602/43, 602/48, 63; 604/174, 175, 265, 513, 539, 604/8, 288.01, 337, 532, 534; 606/108, 191; 600/208, 201, 29, 30, 32; 128/838, 840, 128/859, 846, 887, 888, 885
See application file for complete search history.

(56) References Cited

U.S. PATENT DOCUMENTS

| | | | |
|---|---|---|---|
| 4,581,020 A | 4/1986 | Mittleman | |
| 4,676,782 A | 6/1987 | Yamamoto et al. | |
| 4,897,081 A | 1/1990 | Poirier et al. | |
| 5,064,415 A | 11/1991 | Walder et al. | |
| 5,108,430 A * | 4/1992 | Ravo | ............ 623/23.68 |
| 5,207,652 A | 5/1993 | Kay | |
| 6,004,329 A | 12/1999 | Myers et al. | |
| 6,074,380 A | 6/2000 | Byrne et al. | |
| 6,551,346 B2 | 4/2003 | Crossley | |
| 6,607,504 B2 | 8/2003 | Haarala et al. | |
| 2004/0054353 A1* | 3/2004 | Taylor | .................. 606/1 |
| 2005/0085791 A1 | 4/2005 | Shaw et al. | |
| 2006/0094998 A1 | 5/2006 | Gorton | |

FOREIGN PATENT DOCUMENTS

| | | |
|---|---|---|
| EP | 1 245 247 A1 | 10/2002 |
| WO | WO 93/07928 | 4/1993 |

(Continued)

OTHER PUBLICATIONS

Baird Holmes, Sue et al., "Skeletal Pin Site Care," Orthopaedic Nursing, Mar./Apr. 2005, pp. 99-106, vol. 24, No. 2, Lippincott Williams & Wilkins, USA.

(Continued)

*Primary Examiner*—Patricia M Bianco
*Assistant Examiner*—Keri J Nicholson
(74) *Attorney, Agent, or Firm*—Hunton & Williams LLP

(57) ABSTRACT

A transcutaneous access shield with an instrument opening and surrounding wall to prevent infection during surgical and other medical procedures. The shield resists the entry of microbes from the skin at the body access point. A shield positioner and skin hook can be used to improve placement of the shield.

21 Claims, 6 Drawing Sheets

FOREIGN PATENT DOCUMENTS

| WO | WO 98/25554 | 6/1998 |
|---|---|---|
| WO | WO 01/87416 A1 | 11/2001 |
| WO | WO 2005/027989 A1 | 3/2005 |
| WO | WO 2006/045608 A2 | 5/2006 |

OTHER PUBLICATIONS

"National Nosocomial Infections Surveillance (NNIS) System Report, data summary from Jan. 1992 through Jun. 2004, issued Oct. 2004," American Journal of Infection Control, Dec. 2004, pp. 470-485, vol. 32, No. 8, Elsevier, Inc., USA.

Jeske, MD, Christian et al., "Early Identification of Bacteria Leading to Central Venous Catheter Contamination," Anesthesia & Analgesia, 2003, pp. 940-943, vol. 97, Lippincott Williams & Wilkins, USA.

Prielipp, MD, FCCM, Richard C. et al., "Skin: The First Battlefield," Anesthesia & Analgesia, 2003, pp. 933-935, vol. 97, Lippincott Williams & Wilkins, USA.

McGee, MD, David C. et al., "Preventing Complications of Central Venous Catheterization," The New England Journal of Medicine, Mar. 20, 2003, pp. 1123-1133, vol. 348, No. 12, Massachusetts Medical Society, Waltham, MA.

O'Grady, MD, Naomi P. et al., "Guidelines for the Prevention of Intravascular Cathether-Related Infections, " MMWR Recommendations and Reports, Aug. 9, 2002, pp. 1-37, vol. 51 (RR10), Centers for Disease Control, Atlanta, GA.

Livesley, M.A. et al., "Use of Pulsed Field Gel Electrophoresis to Determine the Source of Microbial Contamination Central Venous Catheters," European Journal of Clinical Microbiology & Infectious Diseases, 1998, pp. 108-112, vol. 17, Springer, Berlin/Heidelberg, Germany.

Elliott, T.S.J. et al., "Novel Approach to Investigate a Source of Microbial Contamination of Central Venous Catheters," European Journal of Clinical Microbiology & Infectious Diseases, 1997, pp. 210-213, vol. 16, No. 3, Springer, Berlin/Heidelberg, Germany.

Allan, Andrew et al., "Development of a polyurethane percutaneous access device for long-term vascular access," ASAIO Journal, 1990, pp. 349-351, vol. 36, No. 3, Lippincott Williams & Wilkins, USA (abstract only).

* cited by examiner

FIG. 3
FIG. 4
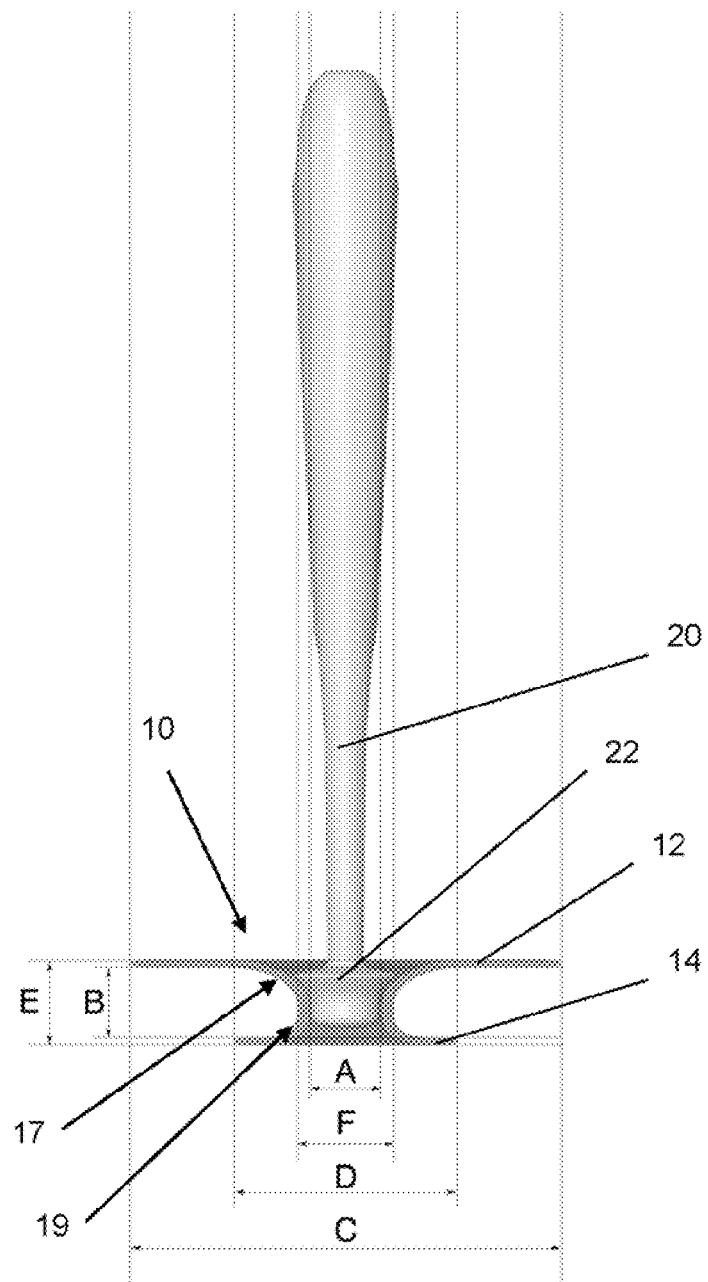
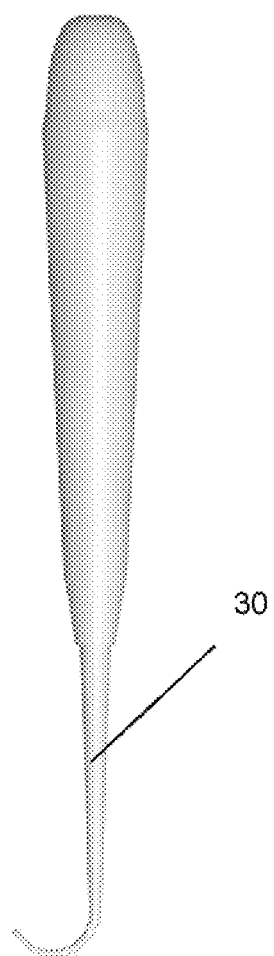

FIG. 8
FIG. 9
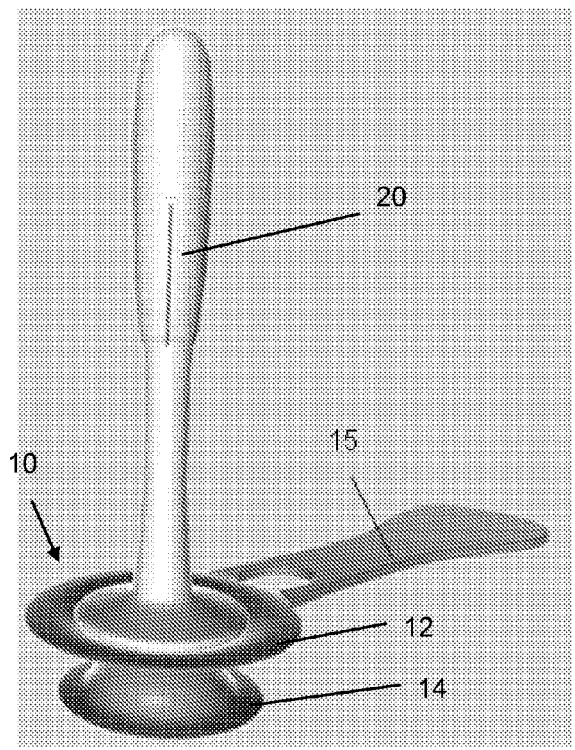
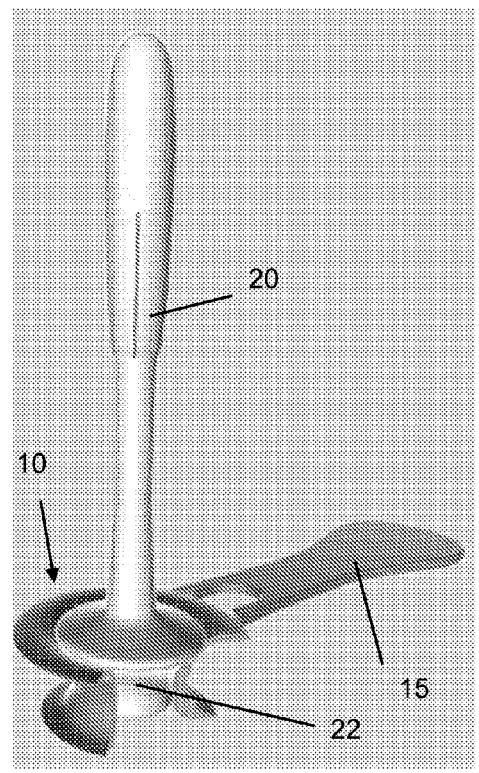

ANTIMICROBIAL TRANSCUTANEOUS ACCESS SHIELD AND KIT

CROSS-REFERENCE TO RELATED APPLICATIONS

This application claims the benefit of U.S. provisional application No. 60/882,299 filed Dec. 28, 2006, which is incorporated herein by reference in its entirety.

BACKGROUND OF THE INVENTION

The present invention is directed to an apparatus, kit and method for preventing infection associated with transcutaneous access during medical and surgical procedures. Typical antimicrobial medical and surgical preparation procedures, such as preparation for accessing blood vessels with catheters and other invasive instruments, attempt to reduce the incidence of infection by seeking to eliminate microbes at the skin's surface. However, studies have confirmed that over 20% of microbes reside under the skin's surface, such as in the pores and skin appendages (e.g. hair follicles, sweat glands, sebaceous glands, and the like), where topical preparations cannot adequately penetrate. Elegant research has shown that microbes are present on and in the skin and skin structures after even the most thorough preparation. Research has also shown that it is these microbes that are responsible for most of the catheter related bloodstream infections. The microbes are introduced during insertion of the catheters and while the catheters are left in place as a result of direct contact of the instruments and catheter with the skin. The present invention thus seeks to reduce the incidence of bloodstream infections arising from such access and thereby reduce morbidity, mortality, and healthcare costs.

In 2002, the Centers for Disease Control and Prevention published guidelines in its Morbidity and Mortality Weekly Report in which they outline steps to minimize blood stream infections. The guidelines indicate that in American intensive care units, the average infection rate for central venous catheters is 5.3 per 1000 catheter days. At 15 million catheter days per year, there are an estimated 80,000 preventable infections per year. The mortality rate with these infections ranges from 0% to 35%. Additional costs range from $34,508 to $56,000 per infection for an annual total of $296 million to $2.3 billion. When entire hospitals are considered, there are an estimated 250,000 catheter related bloodstream infections per year with mortality rates of 12% to 25% and a cost of $25,000 per infection.

U.S. Pat. No. 6,074,380 to Byrne et al., incorporated herein by reference, discloses one attempt to reduce the risks of such infections in transcutaneous surgery though the use of a shallow dish-shaped shield device with an instrument access port. However, the Byrne et al. shield device is a bulky, funnel-type apparatus that is not practical or easy to position and use. Further, the Byrne et al. device is relatively complex to manufacture.

Accordingly there is a need for an inexpensive, easy-to-manufacture and easy-to-position shield apparatus that resists infection during surgical access into the body of humans and animals, including vascular procedures, orthopedic procedures, organ access, neurosurgery, catheter/tubing insertion, arthroscopic procedures, cosmetic surgeries (e.g. liposuction) and the like.

SUMMARY OF THE INVENTION

To answer these needs, the present invention provides in one embodiment a shield device that isolates and shields microbes left on and in the skin and skin structures (after typical antiseptic preparation) from instruments accessing the body, including surgical tools, tubes, intravascular catheters and the like, during the insertion and/or leaving in place of the instruments. In other embodiments the shield device may include other shapes with an instrument opening, dependent on the necessary application and access point to the body. It will be appreciated that embodiments of the present invention may be employed in both human and veterinary medical and surgical procedures.

In embodiments of the invention including a shield for indwelling vascular access catheters, a shield may be used either only during the procedure of insertion or it may be left in place for an extended period of time. A shield left in place protects from bloodstream infections by preventing "pistoning" action at skin's surface of a catheter placed through the skin by the shield anchoring itself to the catheter and to the skin. In various embodiments, anchoring between the catheter and shield is facilitated by adhesives, surface friction, mechanical securing means and the like. Antimicrobial materials comprising, impregnating and/or coating the shield will also be appreciated to further protect from infection when the shield is used in conjunction with a catheter.

It is therefore an objective of the invention to reduce the incidence of bloodstream infections to reduce morbidity, mortality, and healthcare costs.

It is a further objective to eliminate all contact of the instruments with microbes that cause the infections.

In embodiments of the invention a shield of the present invention includes an aperture with top and bottom frustum portions with a narrow midsection, such as an hourglass-type shape. Such frustum portions with larger diameters than a narrow midsection provide enhanced access angles for needles and instruments through the aperture.

In an embodiment, an apparatus of the invention is used in conjunction with standard central vascular access technique (Seldinger technique). It will be appreciate that the invention can also be used with all vascular access catheters and may be scaled to accommodate catheters of different sizes, as well as in adult, pediatric and veterinary applications.

In some embodiments an apparatus of the invention is made from a semi-rigid plastic for ease of manufacture and disposability. In embodiments of the invention an antimicrobial is impregnated, sprayed or coated in or on the device. It will be appreciated that an other embodiments, an apparatus of the invention may be manufactured from various polymers and metals, including antimicrobial materials.

In one embodiment of the invention, a handle with a shield positioner and hook are provided to ease placement of the shield device. The positioner, hook and shield device may be packaged as a sterile unit or as part of kit, such as catheter kit. In other embodiments a positioner, hook and shield device may be individually provided in separate sterile packages and usable with each of the other components as necessary.

In further embodiments, a shield device of the present invention may be semi-transparent to allow for visualization of the skin edge to monitor the wound, particularly for infections.

A further objective of the invention, in one embodiment, is to permit the shield device to be left in place for the entire period of short-term or long-term catheter use.

In a further embodiment of the invention, a shield device reduces the incidence of infection associated with orthopedic external fixation procedures. In such embodiments, the invention protects the skin from trauma related to the insertion of the pins or screws, thereby making the skin less susceptible to microbial overgrowth.

In still further embodiments, a shield device of the present invention includes perforations, creases or similar deconstruction means, permitting the shield to be removed from the access site, including removable from around a catheter or similar instrument that might remain in place at an access site.

BRIEF DESCRIPTION OF DRAWINGS

FIG. 3 is a front partial cross-sectional view of a shield positioner and shield device in an embodiment of the present invention.

FIG. 4 is front view of a hook device in an embodiment of the present invention.

FIG. 8 is a front perspective view of a shield positioner and shield device with handle in an embodiment of the present invention.

FIG. 9 is a front perspective partial cutaway view of a shield positioner and shield device with handle in an embodiment of the present invention.

DETAILED DESCRIPTION THE INVENTION

Figure 1:
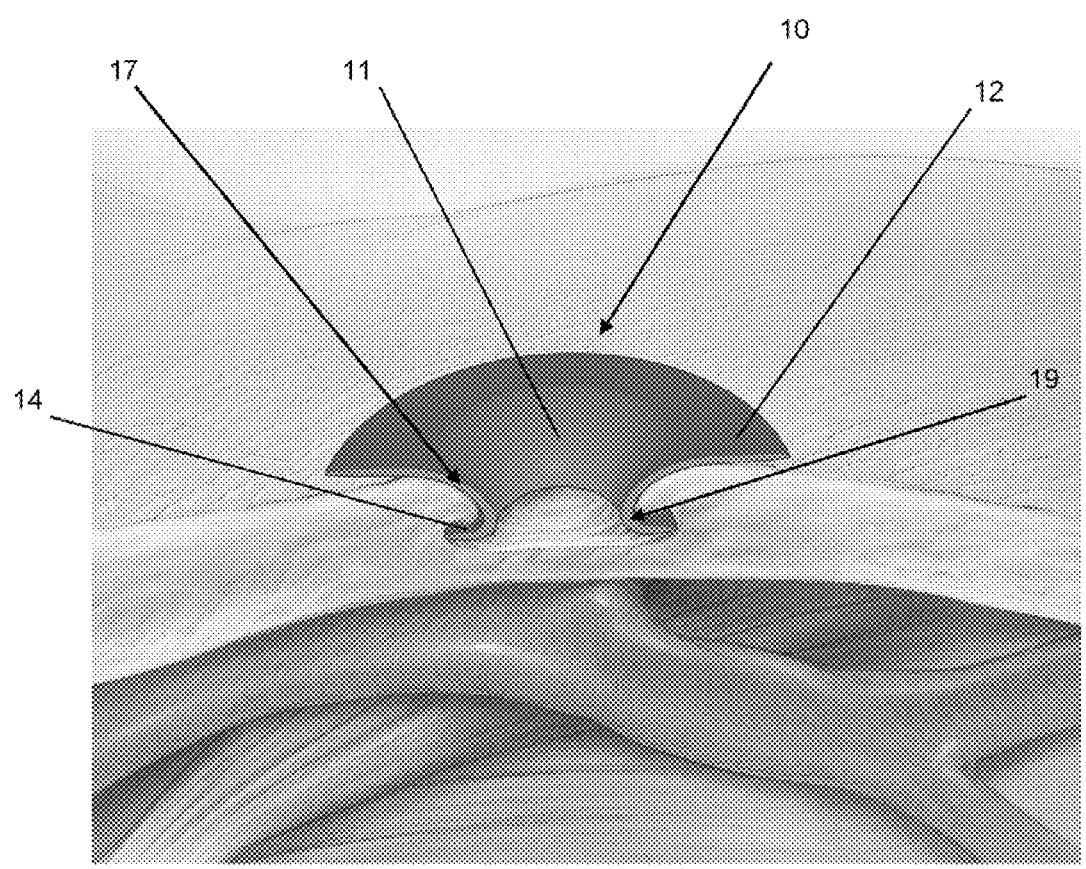
FIG. 1 is a cross-section perspective view of a shield device inserted for transcutaneous access in an embodiment of the present invention.

In embodiments, the present invention provides an apparatus and related methods for providing a shield that resists infection-causing microbes that may enter the body during human and veterinary surgical and other medical procedures requiring transcutaneous access and introduction of instruments that might otherwise contact such microbes in the skin or skin structures.

Although depicted embodiments of the invention are particularly well-suited for use in providing catheter access to blood vessels, such as a central venous catheter, the invention is not intended to be limited solely thereto and may be utilized with various instruments and medical procedures, including orthopedic external fixation hardware, neurosurgery and shunt access, arthroscopic procedures, cosmetic surgery (including liposuction), long and short-term catheters, implants, and other access points into the body with a high risk of infection.

Accordingly, it will be appreciated that a shield device and related depicted optional components, such as a shield positioner and hook device, of the present invention may include different sizes (including adult, pediatric or veterinary), different shapes that include an aperture for body access, and may be manufactured from different medical grade materials. In embodiments of the invention, medical grade plastics (such as PVC, polyutherane and the like) provide cost-efficient manufacturing materials for an apparatus of the present invention. In certain embodiments, the shield device may be constructed of flexible materials to facilitate placement. In other embodiments, medical grade metals may be utilized.

Different colors may be used to improve visualization of the access point for a procedure and/or for signifying information associated with a procedure such as the individual who inserted the shield 10, when a shield 10 (and e.g. catheter) was inserted, and the like. Further, a transparent or semi-transparent shield 10 may be used to permit monitoring of the underlying wound. Antimicrobial agents may also be utilized in the manufacture such as impregnation and/or coating of a shield device and related components, including the use of antimicrobial polymers, metals, and the like. Further, in embodiments of the invention, antimicrobial gels, ointments and other wound/opening preparation agents may be applied in conjunction with a shield device of the present invention.

In various embodiments of the invention, a shield apparatus and optional related components such as a shield positioner, hook device and/or catheter, may all be disposable and provided in sterile packaging as a kit, may be packaged with other instruments (such as a catheter kit), or may be individually packaged and used together as necessary for a particular medical application.

In other embodiments of the invention a shield device 10 and positioner 20 may include adjustable components. For example, a shield device 10 may be provided with retractable periphery and/or adjustable aperture wall 11 by conventional means. A positioner 20 may include an adjustable handle length.

Referring to FIG. 1, in one embodiment of the invention, shield device 10 includes an aperture for providing a transcutaneous access point during a surgical or medical procedure in which an instrument is introduced into the body. In the depicted embodiment, shield device 10 comprises a wall 11 surrounding an aperture. In embodiments of the invention providing improved access angles for needles and other instruments over a cylindrical shape, the aperture wall defines top conical frustum portion 17 and bottom conical frustum portion 19 with a narrow midsection of the aperture, like an hourglass-type shape. In embodiments, an upper protruding brim 12 and lower protruding brim 14 facilitate holding and shielding the surrounding skin and infection-causing microbes therein from the access point. In embodiments of the invention, the shield device 10 is particularly well-suited for insertion of a central venous catheter that may require long or short-term insertion.

In an embodiment of the invention shown in FIG. 1, the upper protruding brim of shield 10 covers the surface of the epidermis around the periphery of the aperture and access point. Accordingly, the upper protruding brim 12 shields instruments from contamination by unwanted touching of the surrounding skin at the access point into the body, such as insertion of a catheter into a vein. Further, the upper 12 and lower 14 protruding brims of shield 10 better stabilize the outer surrounding skin for keeping the shield 10 in place over other prior art shields (such as disclosed in U.S. Pat. No. 6,074,380).

It will be appreciated that a surgical incision may be made at the desired access point and the shield device 10 inserted and situated manually by hand and/or with known tools such as forceps and the like.

Figure 2A:
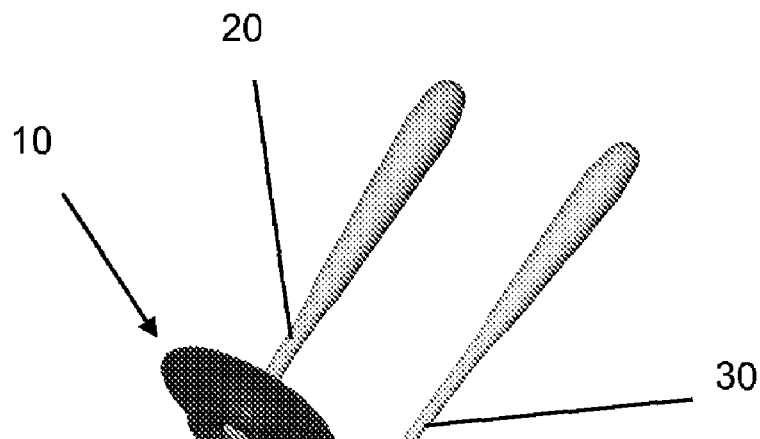
FIGS. 2A-2C are perspective views of a shield device and shield positioner depicting insertion of the shield device into the skin in an embodiment of the present invention.
Figure 2B:
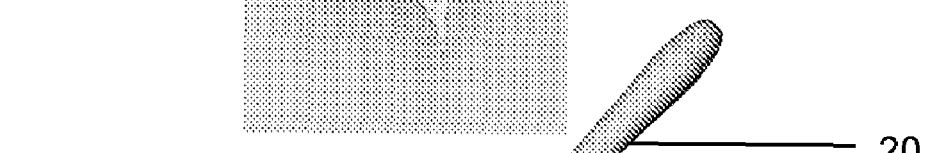
Figure 2C:
Figure 2C:
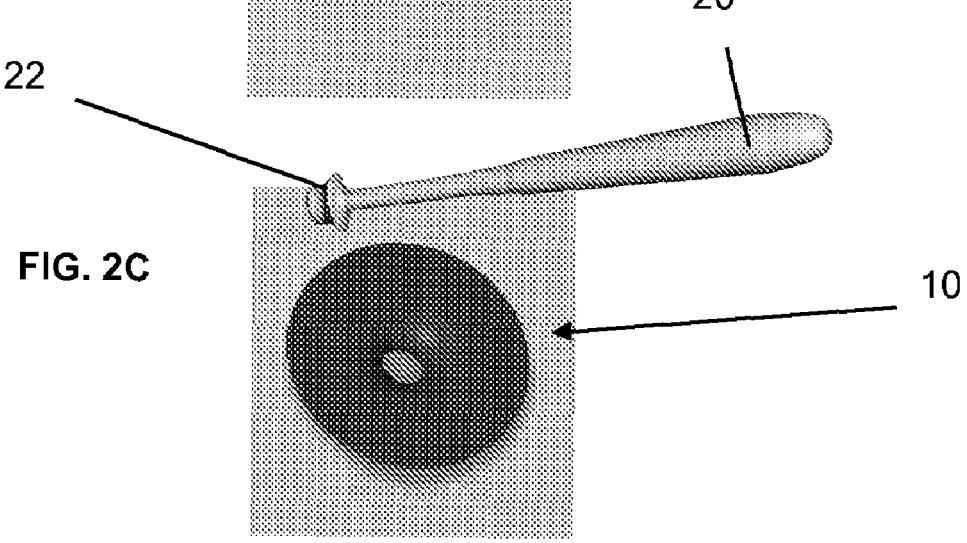
Figure 5:
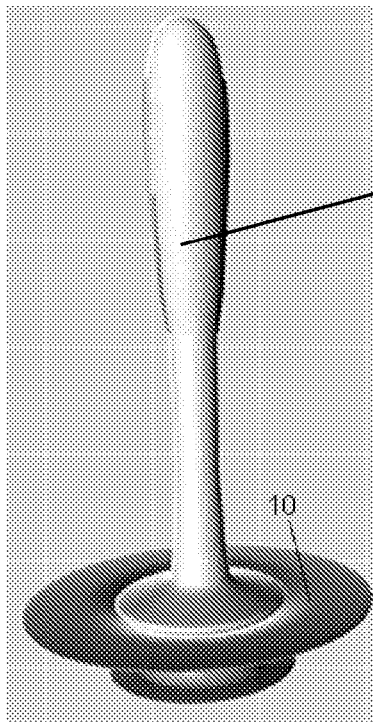
FIG. 5 is a front perspective view of a shield positioner and shield device in an embodiment of the present invention.
Figure 6:
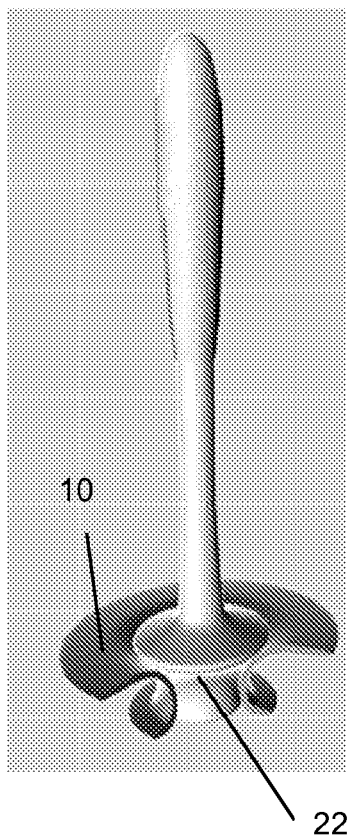
FIG. 6 is a front perspective partial cutaway view of a shield positioner and shield device in an embodiment of the present invention.
Figure 7:
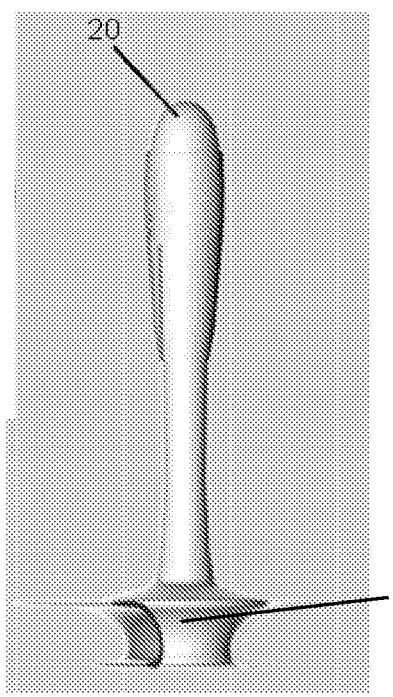
FIG. 7 is a front partial cutaway view of a shield positioner and shield device in an embodiment of the present invention.
Figure 10:
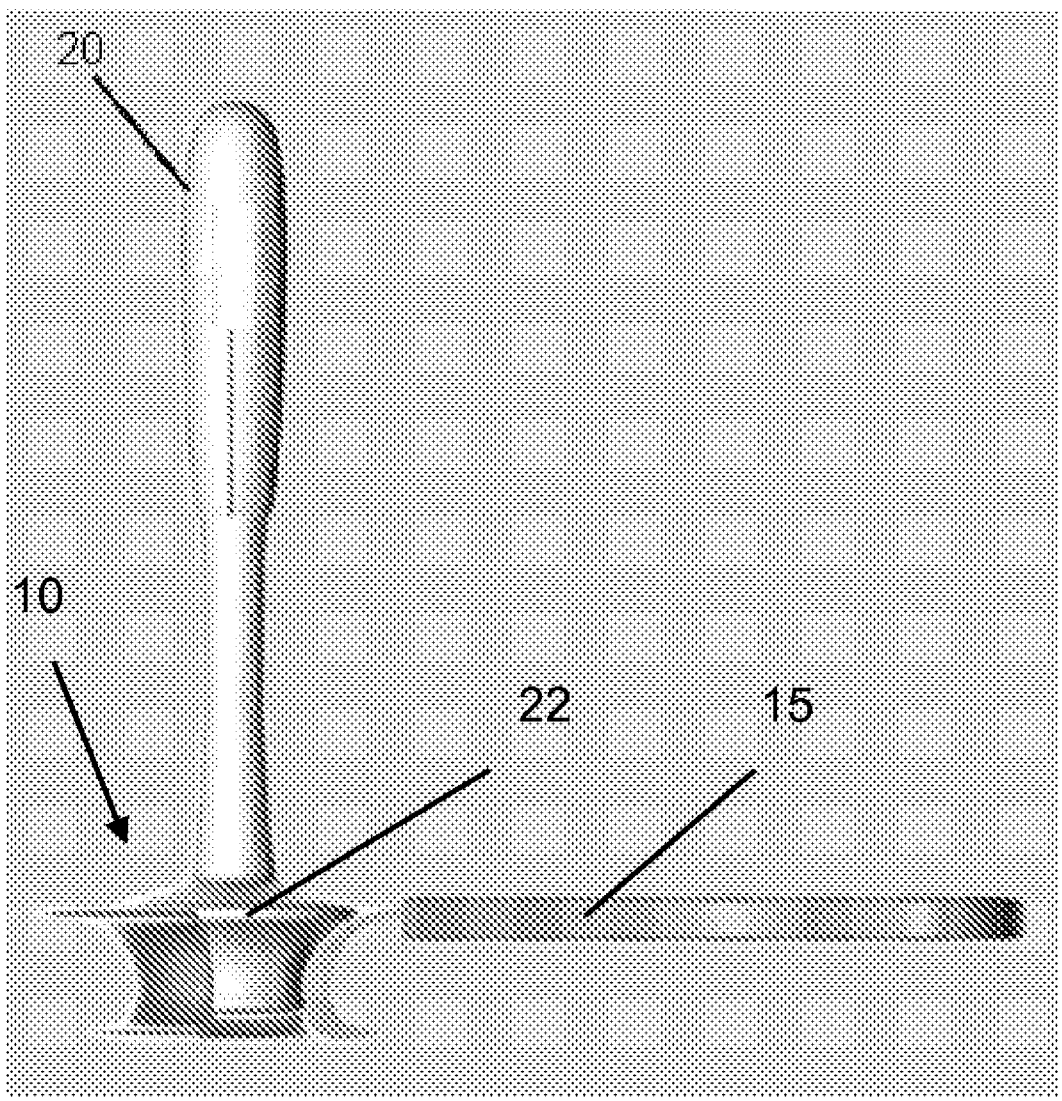
FIG. 10 is a front partial cutaway view of a shield positioner and shield device with handle in an embodiment of the present invention.

With specific reference to FIGS. 2A through 2C, and further reference to FIGS. 3-10, in other embodiments, shield device 10 may be inserted and situated with a shield positioner 20. In further embodiments a hook 30 may also be provided, although not required, to retract the skin at the access point and facilitate insertion and positioning of the shield device 10. It will be appreciated that in some embodiments the shield device 10 may be positioned with only one or both of the shield positioner 20 and hook 30. In further embodiments the shield 10 may be provided with an integral or detachable handle 15.

In one embodiment of the invention, a procedure utilizing a shield device 10 is as follows:

1: The access site is chosen (subclavian, internal jugular, femoral)

2: Skin is prepared using antimicrobial skin prep of choice and drape is placed.

3: Anatomic landmarks are carefully identified.

4: Skin incision is made.

5: Hook 30 is used to elevate an edge of skin. (FIG. 2A)

6: Bottom protruding brim (or flange) 14 of shield device 10 is placed under skin with positioner device 20. (FIG. 2B)

7: Hook 30 is used to elevate opposite edge of skin. (FIG. 2B)

8: Bottom protruding brim (or flange) 14 of shield 10 is placed under second edge of skin thereby securing the device with upper protruding brim (or flange) 12 secured over the skin surface. (FIG. 2C)

9: Seldinger technique is then used through the aperture defined by aperture wall 11 to access vessel and place catheter.

It will be appreciated that these steps in conjunction with shield 10 eliminate any contact of the tools or catheter with microbes left after the skin prep.

In embodiments of the invention a shield may be left in place with a catheter for an extended period of time to protect from bloodstream infections by preventing "pistoning" action at skin's surface of a catheter placed through the skin by the shield anchoring itself to the catheter and to the skin. In various embodiments, anchoring between the catheter and shield is facilitated by adhesives, surface friction, mechanical securing means and the like. Antimicrobial materials comprising, impregnating and/or coating the shield will also be appreciated to further protect from infection when the shield is used in conjunction with a catheter.

With further reference to FIG. 3, in one embodiment of the invention a shield device may include the following non-limiting illustrative dimensions by letter reference: (A) about 2.5 to 3.5 mm; (B) about 2.5 to 3.5 mm; (C) about 17 to 19 mm; (D) about 8.5 to 9.5 mm; (E) about 3.25 to 4.0 mm; (F) about 3.5 to 4.5 mm.

With further reference to FIGS. 3 and 5-10, in embodiments of the invention positioner 20 is provided with a head 22 contoured to engage aperture wall 11 of shield device. In one depicted embodiment positioner head 22 includes a protruding brim portion and tapered portion contoured for releasably engaging the aperture wall 11 of shield 10. In one non-limiting embodiment positioner 20 includes a handle length from end tip to brim of head 22 of about 50 to 50 mm and a protruding brim diameter length of head 22 of about 10 to about 11 mm. In one non-limiting embodiment positioner head 22 is a frustum portion tapering from a protruding brim along a length of about 4 to 5 mm to the head tip. In a non-limiting embodiment the head tip of positioner head 22 includes a diameter of about 3 to 4 mm.

It will be appreciated that in other non-limiting embodiments positioner 20 may be provided other conventional releasable engagement means in conjunction with shield 10, such as a retractable head portion, releasable grips and the like.

Accordingly, the present invention is not confined to the structures and process described in the foregoing description, but is intended to include those embodiments within the full scope of the following claims.

What is claimed is:

1. A shield device for preventing infection at a transcutaneous access point of a human or animal body comprising:
    an at least semi-rigid wall defining an open aperture with a first frustum portion, midsection portion and second frustum portion, wherein the midsection portion of the aperture includes a more narrow opening than end openings of each frustum portion;
    a top continuous solid surface brim protruding outward from an end opening of the first frustum portion, wherein the top continuous solid surface includes a top continuous outer edge periphery that substantially lies in a first plane; and
    a bottom continuous solid surface brim protruding outward from an end opening of the second frustum portion, wherein the bottom continuous solid surface includes a bottom continuous outer edge periphery that substantially lies in a second plane.

2. The shield device of claim 1, further comprising an antimicrobial agent.

3. The shield device of claim 1, wherein said top continuous solid surface brim has a larger diameter than the bottom continuous solid surface brim.

4. The shield device of claim 1, wherein said device includes a detachable handle and is disposable.

5. The shield device of claim 1, further comprising at least one of a transparent and semi-transparent material.

6. The shield device of claim 1, wherein the top continuous solid surface brim has a greater surface area than the bottom continuous solid surface brim.

7. The shield device of claim 1, wherein the first and second planes are substantially parallel.

8. The shield device of claim 1, wherein the end openings are from about 3.5 to 4.5 mm wide and the more narrow opening of the midsection portion is from about 2.5 mm to less than 3.5 mm wide.

9. The shield device of claim 1, wherein the top and bottom continuous edge peripheries are circular.

10. The shield device of claim 1, further comprising a flexible material.

11. A shield kit for preventing infection at a transcutaneous access point of a human or animal body comprising:
    a shield device including an at least semi-rigid wall defining an open aperture with first and second frustum portions of the aperture each having a larger opening than an opening at a midsection of the aperture;
    a top continuous solid surface brim protruding outward from an end opening of the first frustum portion of the shield device, wherein the top continuous solid surface brim includes a top continuous outer edge periphery that substantially lies in a first plane;
    a bottom continuous solid surface brim protruding outward from an end opening of the bottom frustum portion of the shield device, wherein the bottom continuous solid surface brim includes a bottom continuous outer edge periphery that substantially lies in a second plane; and
    a positioner with a head including a tapered portion contoured to releasably engage within the aperture of the shield device.

12. The kit of claim 11, wherein said tapered portion of the head of the positioner includes a frustum portion tapering along a length to a tip of the head.

13. The kit of claim 12, wherein said head of the positioner includes a protruding brim having a complementary shape to the end opening of the first frustum portion of the shield device.

14. The kit of claim 13, wherein one or more of the shield device and positioner are disposable.

15. The kit of claim 11, further comprising a hook device.

16. The kit of claim 15, wherein one or more of the shield device, positioner and hook device are disposable.

17. The kit of claim 11, further comprising a catheter.

18. The kit of claim 15, further comprising a catheter.

19. The kit of claim 11, wherein said head of the positioner includes a protruding brim having a complementary shape to the end opening of the first frustum portion of the shield device.

20. A method for reducing incidence of infection during a transcutaneous medical procedure comprising:
    incising skin at a desired access point;
    elevating a first edge of the incised skin;
    placing a first portion of a bottom protruding continuous solid surface brim having a continuous outer edge periphery substantially in a single plane and surrounding a bottom end opening of a first frustum portion of an open aperture of an at least semi-rigid shield under the first edge of the incised skin;
    elevating an opposite second edge of skin; and
    placing a second portion of the bottom protruding continuous solid surface brim of the shield under the second edge of skin thereby securing a top protruding solid surface brim having a continuous outer edge periphery substantially in a single plane and surrounding a top end opening of a second frustum portion of an open aperture of the shield over the surface of the skin.

21. The method of claim 20 further comprising positioning the shield with a removable positioner engaging a top end opening of the shield.

* * * * *